(12) United States Patent
Salazar et al.

(10) Patent No.: US 6,184,382 B1
(45) Date of Patent: Feb. 6, 2001

(54) PROCESS FOR PREPARING N6-SUBSTITUTED ADENOSINE DERIVATIVES

(75) Inventors: Diane C. Salazar, deceased, late of Wayne, by Richard Salazar; Walter Rodriguez, Douglasville, both of PA (US); James P. Sherbine, Voorhees, NJ (US); Rick G. Woodward, Harleysville, PA (US); Adam W. Sledeski, Collegeville, PA (US); Matthew R. Powers, Barto, PA (US); Michael K. O'Brien, Berwyn, PA (US)

(73) Assignee: Aventis Pharmaceuticals Products Inc., Collegeville, PA (US)

( * ) Notice: Under 35 U.S.C. 154(b), the term of this patent shall be extended for 0 days.

(21) Appl. No.: 09/481,979

(22) Filed: Jan. 12, 2000

Related U.S. Application Data

(63) Continuation of application No. PCT/US99/29643, filed on Dec. 14, 1999.

(60) Provisional application No. 60/113,077, filed on Dec. 21, 1998.

(51) Int. Cl.$^7$ .................................................. C07D 409/12
(52) U.S. Cl. .................. 546/281.4; 546/118; 546/281.1; 546/307
(58) Field of Search ................. 546/281.4, 307, 546/281.1, 118

(56) References Cited

U.S. PATENT DOCUMENTS 5,652,366 * 7/1997 Spada et al. ..................... 546/118

* cited by examiner

Primary Examiner—Bernard Dentz
(74) Attorney, Agent, or Firm—Irving Newman

(57) ABSTRACT

The invention is directed to improved methods for preparing N6-substituted adenosine derivatives, to intermediates useful therefor and to methods of preparing these intermediates.

18 Claims, No Drawings

PROCESS FOR PREPARING N6-SUBSTITUTED ADENOSINE DERIVATIVES

CROSS REFERENCE TO RELATED APPLICATIONS

This is a continuation of International Patent Application No. PCT/US99/29643, filed Dec. 14, 1999, which is, in turn, a continuation of U.S. patent application Ser. No. 60/113,077 filed Dec. 21, 1998, now abandoned.

TECHNICAL FIELD

This invention is directed to a process for preparing N6-substituted adenosine derivatives, to intermediates useful therefor and to methods of preparing these intermediates.

BACKGROUND OF THE INVENTION

N6-substituted adenosine derivatives, as exemplified by [1S-[1α,2β,3β,4α(S*)]]-4-[7-[[1-[(3-chlorothien-2-yl)methyl]propyl]amino]-3H-imidazo[4,5-b]pyrid-3-yl]N-ethyl-2,3-dihydroxycyclopentanecarboxamide are useful as cardiovascular agents, more particularly as antihypertensive and anti-ischemic agents, as cardioprotective agents which ameliorate ischemic injury or myocardial infarct size consequent to myocardial ischemia, and as an antilipolytic agents which reduce plasma lipid levels, serum triglyceride levels, and plasma cholesterol levels. See U.S. Pat. Nos. 5,364,862 and 5,561,134.

Methods of preparing these N6 adenosine derivatives and intermediates thereto are disclosed in U.S. Pat. Nos. 5,364,862 and 5,561,134 and International Patent Application Nos. PCT/US97/11320, PCT/US97/15729 and PCT/US97/21439.

SUMMARY OF THE INVENTION

This invention is directed to a process for preparing a 2-halo-3-nitro-4-aminopyridine compound of formula

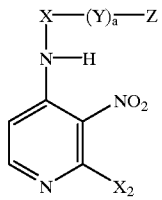

in which a 2,4-dihalo-3-nitropyridine compound of formula

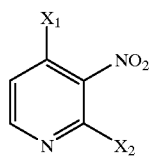

wherein $X_1$ and $X_2$ are independently Cl or F, is reacted with an amine of formula $H_2N-X-(Y)_a-Z$; wherein X is a straight or branched chain alkylene, cycloalkylene or cycloalkenylene group; Y is $NR_4$, O or S; a=0 or 1; and Z is of the formula:

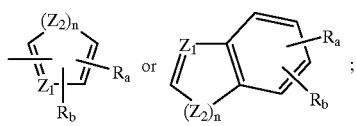

where
$Z_1$ is N, $CR_5$, $(CH)_m\text{-}CR_5$ or $(CH)_m\text{-}N$, m being 1 or 2; $Z_2$ is N, $NR_6$, O or S, n being 0 or 1;
$R_4$, $R_5$ and $R_6$ are independently H, alkyl, aryl or heterocyclyl; and
$R_a$ and $R_b$ are independently H, OH, alkyl, hydroxyalkyl, alkyl mercaptyl, thioalkyl, alkoxy, alkoxyalkyl, amino, alkyl amino, carboxyl, acyl, halogen, carbamoyl, alkyl carbamoyl, aryl or heterocyclyl.

In another aspect, this invention is directed to a process for preparing (R)-N-[1-[(3-chlorothien-2-yl)methyl]propyl]-2-halo-3-nitro-4-pyridinamine, by reacting a 2,4-dihalo-3-nitropyridine, wherein halo is Cl or F with (R)-1-(3-chlorothien-2-yl)-2-aminobutane, hydrochloride.

The reaction products are process intermediate useful in the preparation of 2,3,4-triaminopyridine compounds. The processes of this invention offers improved yields, purity, ease of preparation and/or isolation of intermediates and final product, and more industrially useful reaction conditions and workability over previously disclosed methods of preparation.

DETAILED DESCRIPTION OF THE INVENTION

Definitions of Terms

As used above and throughout the description of the invention, the following terms, unless otherwise indicated, shall be understood to have the following meanings:

"Acyl" means a straight or branched alkyl-C=O group. "Thioacyl" means a straight or branched alkyl-C=S group. Preferred acyl and thioacyl groups are lower alkanoyl and lower thioalkanoyl having from 1 to about 6 carbon atoms in the alkyl group.

"Alkyl" means a saturated aliphatic hydrocarbon group which may be straight or branched and having about 1 to about 20 carbon atoms in the chain. Preferred alkyl groups may be straight or branched and have about 1 to about 10 carbon atoms in the chain. Branched means that a lower alkyl group such as methyl, ethyl or propyl is attached to a linear alkyl chain.

"Lower alkyl" means an alkyl group having 1 to about 6 carbons.

"Cycloalkyl" means an aliphatic ring having 3 to about 10 carbon atoms in the ring. Preferred cycloalkyl groups have 4 to about 7 carbon atoms in the ring.

"Carbamoyl" means an

group. Alkylcarbamoyl and dialkylcarbamoyl means that the nitrogen of the carbamoyl is substituted by one or two alkyl groups, respectively.

"Carboxyl" means a COOH group.

"Alkoxy" means an alkyl-O group in which "alkyl" is as previously described. Lower alkoxy groups are preferred. Exemplary groups include methoxy, ethoxy, n-propoxy, i-propoxy and n-butoxy.

"Alkoxyalkyl" means an alkyl group, as previously described, substituted by an alkoxy group, as previously described.

"Alkoxycarbonyl means an alkoxy-C=O group.

"Aralkyl" means an alkyl group subsituted by an aryl radical, wherein "aryl" means a phenyl or naphthyl. "Substituted aralkyl" and "substituted aryl" means that the aryl group, or the aryl group of the aralkyl group is substituted with one or more substituents which include alkyl, alkoxy, amino, nitro, carboxy, carbalkoxy, cyano, alkyl amino, halo, hydroxy, hydroxyalkyl, mercaptyl, alkylmercaptyl, trihaloalkyl, carboxyalkyl or carbamoyl.

"Aralkoxycarbonyl" means an aralkyl-O—C=O group.

"Aryloxycarbonyl" means an aryl-O—C=O group.

"Carbalkoxy" means a carboxyl substituent esterified with an alcohol of the formula $C_nH_{2n+1}OH$, wherein n is from 1 to about 6.

"Halogen" (or "halo") means chlorine (chloro), fluorine (fluoro), bromine (bromo) or iodine (iodo).

"Heterocyclyl" means about a 4 to about a 10 membered ring structure in which one or more of the atoms in the ring is an element other than carbon, e.g., N, O or S. Heterocyclyl may be aromatic or non-aromatic, i.e., may be saturated, partially or fully unsaturated. Preferred heterocyclyl groups include pyridyl, pyridazinyl, pyrimidinyl, isoquinolinyl, quinolinyl, quinazolinyl, imidazolyl, pyrrolyll, furanyl, thienyl, thiazolyl, benzothiazolyl, piperidinyl, pyrrolidinyl, tetrahydrofuranyl, tetrahydropyranyl, and morpholinyl groups.

"Substituted heterocyclyl" means that the heterocyclyl group is substituted by one or more substituents wherein the substituents include alkoxy, alkylamino, aryl, carbalkoxy, carbamoyl, cyano, halo, heterocyclyl, trihalomethyl, hydroxy, mercaptyl, alkylmercaptyl or nitro.

"Hydroxyalkyl" means an alkyl group substituted by a hydroxy group. Hydroxy lower alkyl groups are preferred. Representative groups include hydroxymethyl, 2-hydroxyethyl, 2-hydroxypropyl and 3-hydroxypropyl.

Preferred Embodiments

The preparation of N6-substituted adenosine derivatives of formula (I) is outlined in Scheme 1.

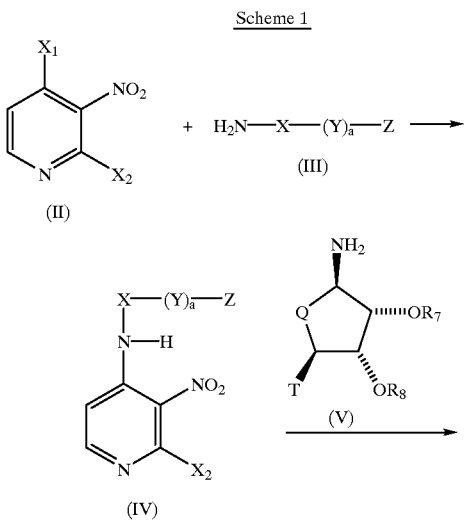

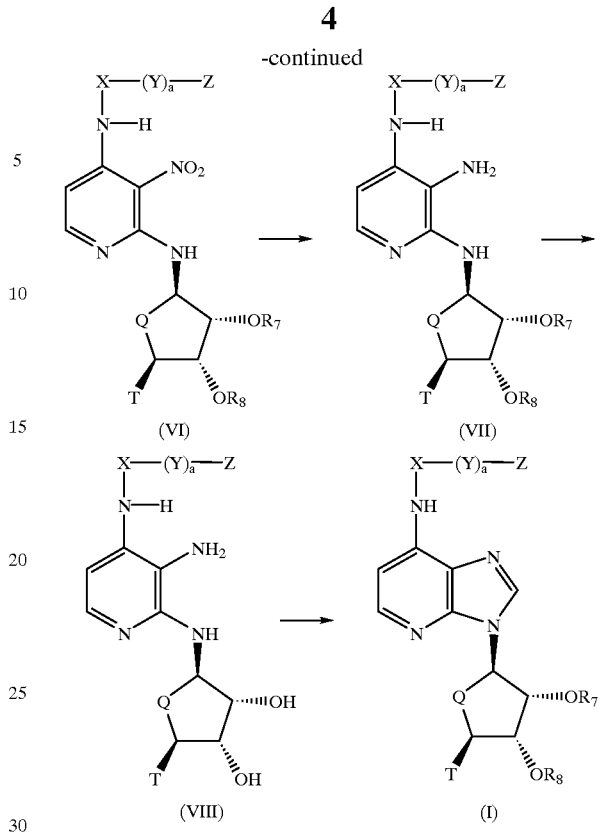

In Scheme 1, $X_1$ and $X_2$ are independently Cl or F,
Q is $CH_2O$;
T is

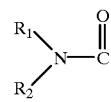

or $R_3O$—$CH_2$;
X is a straight or branched chain alkylene, cycloalkylene or cycloalkenylene group;
Y is $NR_4$, O or S;
a=0 or 1;
Z is of the formula

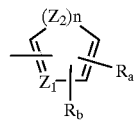

or

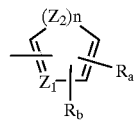

;

$Z_1$ is N, $CR_5$, $(CH)_m$-$CR_5$ or $(CH)_m$-N, m being 1 or 2;
$Z_2$ is N, $NR_6$, O or S, n being 0 or 1;
$R_1$, $R_2$, $R_3$, $R_4$, $R_5$ and $R_6$ are independently H, alkyl, aryl or heterocyclyl;
$R_7$ and $R_8$ are independently hydrogen, alkyl, aralkyl, carbamoyl, alkyl carbamoyl, dialkyl-carbamoyl, acyl, alkoxycarbonyl, aralkoxycarbonyl, aryloxycarbonyl, or $R_7$ or $R_8$ together may form

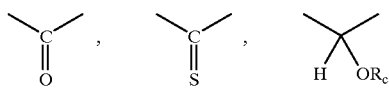

where $R_c$ is hydrogen or alkyl,

where $R_d$ and $R_e$ are independently hydrogen, alkyl, or together with the carbon atom to which they are attached may form a 1,1-cycloalkyl group; and $R_a$ and $R_b$ are independently H, OH, alkyl, hydroxyalkyl, alkyl mercaptyl, thioalkyl, alkoxy, alkoxyalkyl, amino, alkyl amino, carboxyl, acyl, halogen, carbamoyl, alkyl carbamoyl, aryl or heterocyclyl.

As shown in Scheme 1, the preparation of N6-substituted adenosine derivatives of formula (I), begins with the reaction of the 2,4-dihalo-3-nitropyridine compound (II) with an amine of formula $H_2N-X-(Y)_a$-Z (III) provides the 2-halo-3-nitro-4-aminopyridine compound (IV). The reaction is carried out in the presence of a tertiary amine or aromatic amine base such as triethylamine, diisopropylethylamine, pyridine, 4-dimethylaminopyridine, 4-methylmorpholine, and the like or an inorganic carbonate base such as sodium carbonate, potassium carbonate, and the like. Preferred bases are 4-methylmorpholine, triethylamine and diisopropylethylamine. The reaction is carried out in a polar aprotic solvent such as 1-methyl-2-pyrrolidone or dimethylformamide, an aromatic solvent such as benzene or toluene, a higher-boiling ethereal solvent such as diglyme or a hindered alcohol such as isopropanol or 2-butanol at a temperature of from about ambient temperature to the reflux temperature of the solvent. A preferred solvent is 1-methyl-2-pyrrolidone, in which the reaction is carried out at about 35° C.

The 2-halo-3-nitro-4-aminopyridine compound (IV) is then reacted with the protected dihydroxyaminocyclopentane compound (V) using the reaction conditions described above to prepare the 2,4-diamino-3-nitropyridine compound (VI).

Reduction of the 2,4-diamino-3-nitropyridine compound (VI) to the 2,3,4-triaminopyridine compound (VII) is accomplished using methods well known in the art for the reduction of aromatic nitro compounds. Preferred methods for the reduction employ metals such as zinc, iron or tin in the presence of an acidic proton source such as ammonium acetate. Solvents are generally alcohols, preferably methanol or mixtures of alcohols and aromatic solvents such as toluene or benzene. The reduction is preferably accomplished at about ambient temperature. The nitro group is also reduced by catalytic hydrogenation, with platinum catalysts such as $PtO_2$ being preferred.

The groups $R_7$ and $R_8$ are then removed using methods well known in the art to form the 2-N-cyclpentane diol-2,3,4-triaminopyridine compound (VIII). In a preferred aspect of this process, $R_7$ and $R_8$ together form a dimethylacetonide, in which case the acetonide is hydrolyzed with acid using any solvent which is stable to the acid. A preferred method of acetonide hydrolysis uses HCl and methanol at about ambient temperature. The 2-N-cyclpentane diol-2,3,4-triaminopyridine compound (VIII) may be isolated as the acid solution salt, for example as the dihydrochloride salt, or the acid addition salt may be neutralized with base to form the free amine. In a preferred aspect, the 2-N-cyclpentane diol-2,3,4-triaminopyridine compound (VIII) is isolated as its crystalline acid addition salt. In many instances, the properties of the 2-N-cyclpentane diol-2,3,4-triaminopyridine acid addition salt, including ease of crystallization, are controlled by the particular acid counterion. The counterion in the isolated acid addition salt is selected by treating the free amine with the desired acid, or preferably, by employing an acid having the desired counterion in the acid hydrolysis described above.

The 2-N-cyclpentane diol-2,3,4-triaminopyridine compound (VIII) is then cyclized to the N6-substituted adenosine derivative (I) by reaction with formamidine acetate, formic acid or the ortho esters of formic acid as described in U.S. Pat. Nos. 5,364,862 and 5,561,134 and Intern. Pat. App. No. PCT/US97/21439, incorporated herein by reference. Polar aprotic solvents, higher boiling alcohols and esters and aromatic solvents such as toluene have been employed for these types of cyclizations. Esters such as n-propyl and n-butyl acetate or a combination of one of these esters with ethyl acetate are especially preferred. The N6-substituted adenosine derivative (I) is preferably purified by recrystallization from a suitable organic solvent or mixture of organic solvents. Ethyl, n-propyl and n-butyl acetate and propionate are preferred solvents.

In a preferred aspect of the foregoing process,
Q is $CH_2$;
T is

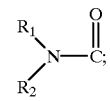

X is a straight or branched chain alkylene;
a=0;
Z is

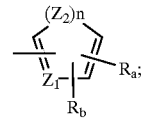

$Z_1$ is N, $CR_5$, $(CH)_m$-$CR_5$ or $(CH)_m$-N, m being 1 or 2;
$Z_2$ is N, $NR_6$, O or S, n being 0 or 1;
$R_1$, $R_2$, $R_3$, $R_4$, $R_5$ and $R_6$ are independently H or alkyl;
$R_7$ and $R_8$ are independently hydrogen or alkyl, or $R_7$ and $R_8$ together may form

where $R_d$ and $R_e$ are independently hydrogen or alkyl, or together with the carbon atom to which they are attached may form a 1,1-cycloalkyl group; and $R_a$ and $R_b$ are independently H, OH, alkyl, hydroxyalkyl, alkyl mercaptyl, thioalkyl, alkoxy, alkoxyalkyl, amino, alkyl amino, carboxyl, acyl, halogen, carbamoyl, alkyl carbamoyl, aryl or heterocyclyl.

In a more preferred aspect, this invention is directed to a process for preparing [1S-[1α,2β,3β,4α(S*)]]-4-[7-[[1-[(3-chlorothien-2-yl)methyl]propyl]amino]-3H-imidazo[4,5-b]

pyrid-3-yl] N-ethyl 2,3-dihydroxycyclopentanecarboxamide as shown in Scheme 2.

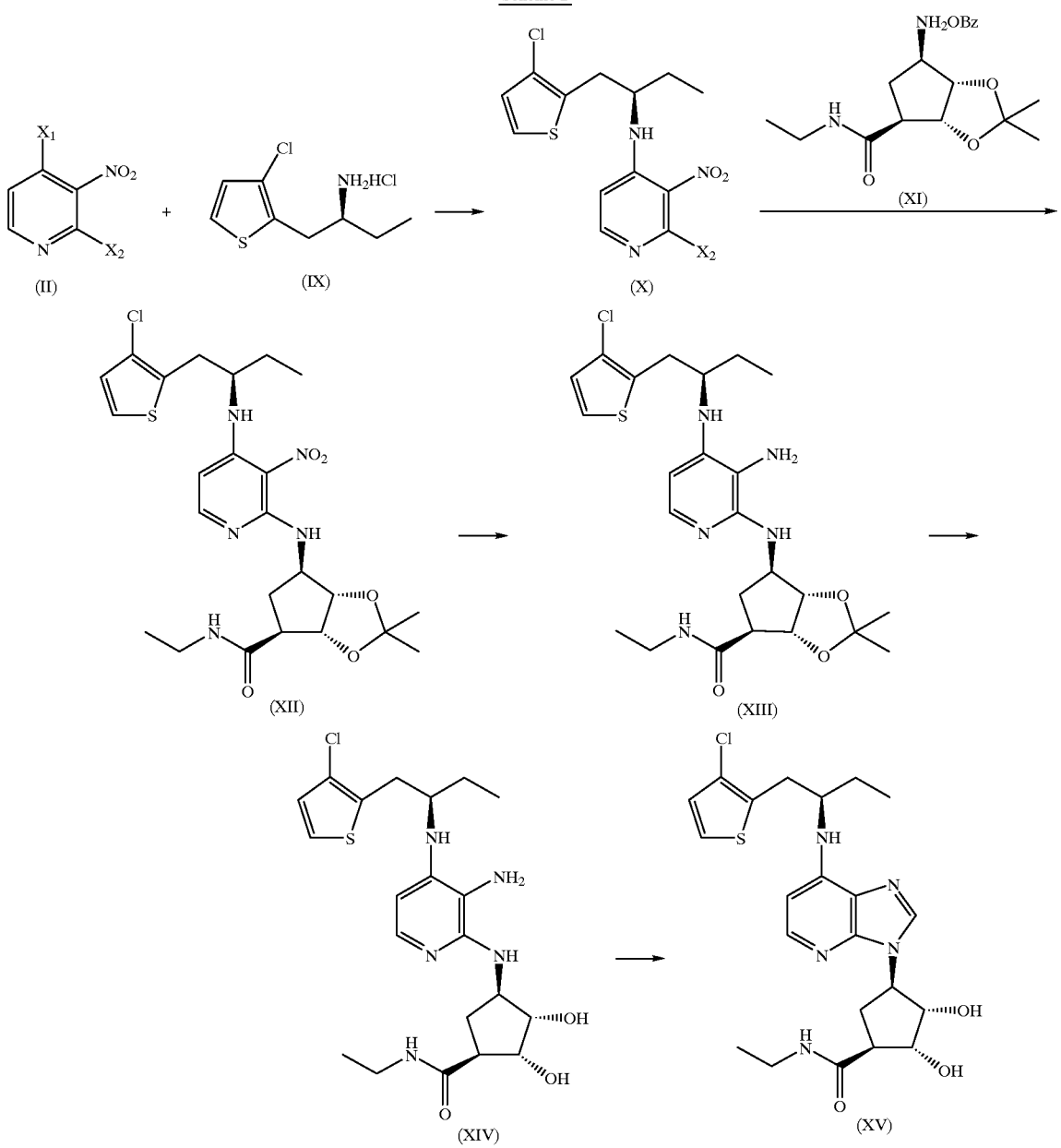

As shown in the foregoing Scheme 2, reaction of the 2,4-dihalo-3-nitropyridine compound (II) with (R)-1-(3-chloro-thienyl-2-yl)-2-aminobutane hydrochloride (IX) using the conditions of base and solvent described in Scheme 1 above provides (R)-N-[1-[(3-chlorothien-2-yl)methyl]propyl]-2-halo-3-nitro-4-pyridinamine (X) ($X_2$ is Cl or F). The reaction is conducted in the presence of excess base to neutralize the hydrochloride salt of (IX), or alternatively, the hydrochloride salt of (IX) is neutralized with base separately, and a solution of the free base (IX) is then mixed with a solution of the 2,4-dihalo-3-nitropyridine compound (II).

Preferred 2,4-dihalo-3-nitropyridine compounds are the compounds of formula (II) wherein $X_1$ is F and $X_2$ is F or Cl, or a mixture thereof, which are prepared by reaction of 2,4-dichloro-3-nitropyridine with a fluorinating agent such as KF.

The (R)-N-[1-[(3-chlorothien-2-yl)methyl]propyl]-2-halo-3-nitro-4-pyridinamine (X) is then reacted with 3aR-[3aα,4α,6a,6aα]-6-amino-N-ethyltetrahydro-3,3-dimethyl-2,4-dioxabicyclo[3.3.0]octan-8-carboxamide benzoate (XI) as described in Scheme 1 above to form [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide (XII) which is then reduced as described in Scheme 1 above to form [3aR-[3aα,4α,6a(R*),6aα]]-6-[4-[[1-[(3-chlorothien-2-yl)methyl]propyl]amino]-3-aminopyrid-2-ylamino]

N-ethyl tetrahydro-2,2-dimethyl-4H-cyclopenta-1,3-dioxole-4-carboxamide (XIII). The reduction is preferably accomplished using zinc, iron or tin in the presence of an acidic proton source such as ammonium acetate, zinc being especially preferred.

Acid hydrolysis of the dimethylacetonide provides [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide. The hydrolysis is preferably accomplished using HCl, in which case crystalline [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentane carboxamide dihydrochloride is isolated directly.

Cyclization of the [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide to form [1S-[1α,2β,3β,4α(S*)]]-4-[7-[[1-[(3-chlorothien-2-yl)methyl]propyl]amino]-3H-imidazo[4,5-b]pyrid-3-yl] N-ethyl 2,3-dihydroxycyclopentane carboxamide (I) is accomplished as described in Scheme 1 above.

In a still more preferred aspect, this invention is directed to a synthesis of [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentane carboxamide dihydrochloride hydrate effected in a concatenated manner without isolation of the intermediate compounds (R)-N-[1-[(3-chlorothien-2-yl)methyl]propyl]-2-halo-3-nitro-4-pyridinamine (X), [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide (XII) and [3aR-[3aα,4α,6a(R*),6aα]]-6-[4-[[1-[(3-chlorothien-2-yl)methyl]propyl]amino]-3-aminopyrid-2-ylamino] N-ethyl tetrahydro-2,2-dimethyl-4H-cyclopenta-1,3-dioxole-4-carboxamide (XIII).

In particular, 2,4-dihalo-3-nitropyridine is reacted with (R)-1-(3-chloro-thienyl-2-yl)-2-aminobutane hydrochloride in a reaction vessel using the condition of base and solvent described above to form a solution of (R)-N-[1-[(3-chlorothien-2-yl)methyl]propyl]-2-halo-3-nitro-4-pyridinamine (X) in the reaction vessel. 3aR-[3aα,4α,6a,6aα]-6-amino-N-ethyltetrahydro-3,3-dimethyl-2,4-dioxabicyclo[3.3.0]octan-8-carboxamide benzoate (XI) and base are then added to the solution in the vessel and the mixture is heated until conversion to [3aR-[3aα,4α,6a(R*),6aα]]-6-[4-[[1-[(3-chlorothien-2-yl)methyl]propyl]amino]-3-nitropyrid-2-yl-amino] N-ethyl tetrahydro-2,2-dimethyl-4H-cyclopenta-1,3-dioxole-4-carboxamide (XII) is essentially complete.

The reaction mixture contained in the vessel is the mixed with water and the aqueous phase, which contains water soluble solvents and impurities, is removed from the vessel.

An alcoholic solvent such as methanol, followed by ammonium acetate and zinc powder, is then added to the organic solution remaining in the vessel and the reaction mixture is heated until reduction of the [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide (XII) to [3aR-[3aα,4α,6a(R*),6aα]]-6-[4-[[1-[(3-chlorothien-2yl)methyl]propyl]amino]-3-aminopyrid-2-ylamino] N-ethyl tetrahydro-2,2-dimethyl-4H-cyclopenta-1,3-dioxole-4-carboxamide (XIII) is essentially complete.

The zinc metal and any other insoluble impurities are then removed by filtration of the contents of vessel and the filtrate is collected in another reaction vessel. Acid hydrolysis of [3aR-[3aα,4α,6a(R*),6aα]]-6-[4-[[1-[(3-chlorothien-2-yl)methyl]propyl]amino]-3-aminopyrid-2-ylamino] N-ethyl tetrahydro-2,2-dimethyl-4H-cyclopenta-1,3-dioxole-4-carboxamide (XIII) is then effected by adding concentrated HCl to the second reaction vessel and heating until conversion to [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide (XIII) is essentially complete. Cooling of the second reaction vessel results in crystallization of [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentane carboxamide dihydrochloride hydrate which is isolated by filtration.

In another still more preferred aspect, this invention is directed to the concatenated synthesis described above further comprising converting 2,4-dichloro-3-nitropyridine to 2,4-difluoro-3-nitropyridine, or a mixture of 2,4-difluoro-3-nitropyridine and 2-chloro-4-fluoro-3-nitropyridine in the reaction vessel $R_1$.

In order to successfully concatenate reaction steps as describe above, solvents and reagents for accomplishing each of the individual reaction steps are selected such that excess reagents and reaction byproducts are readily removed by filtration or extraction, or can remain in the reaction vessel without causing detrimental effects on subsequent reactions performed in the vessel. Accordingly, the following reagents and solvents are preferred.

(1) For conversion of 2,4-dichloro-3-nitropyridine to 2,4-difluoro-3-nitropyridine; KF; tetraphenylphosphonium bromide; 1-methyl-2-pyrrolidinone; toluene.

(1) For conversion of 2,4-dihalo-3-nitropyridine to [3aR-[3aα,4α,6a(R*),6aα]]-6-[4-[[1-[(3-chlorothien-2-yl)methyl]propyl]amino]-3-nitropyrid-2-ylamino]N-ethyltetrahydro-2,2-dimethyl-4H-cyclopenta-1,3-dioxole-4-carboxamide (XII): 1-methyl-2-pyrrolidinone; triethylamine; diisopropylethylamine; 4-methyl morpholine.

(2) For conversion of to [3aR-[3aα,4α,6a(R*),6aα]]-6-[4-[[(1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide (XII) to [3aR-[3aα,4α,6a(R*),6aα]]-6-[4-[[1-[(3-chlorothien-2-yl)methyl]propyl]amino]-3-aminopyrid-2-ylamino] N-ethyl tetrahydro-2,2-dimethyl-4H-cyclopenta-1,3-dioxole-4-carboxamide (XIII): ethyl acetate, methanol, zinc, ammonium acetate.

(3) For conversion of to [3aR-[3aα,4α,6a(R*),6aα]]-6-[4-[[1-[(3-chlorothien-2-yl)methyl]propyl]amino]-3-aminopyrid-2-ylamino] N-ethyl tetrahydro-2,2-dimethyl-4H-cyclopenta-1,3-dioxole-4-carboxamide (XIII) to [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate: ethyl acetate, concentrated HCl.

The concatenated synthesis of [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate described above, in which the intermediate compounds are not isolated but rather are carried forward to the subsequent reaction in solution, minimizes the four step process to two reaction vessels and two filtrations, resulting in a significant reduction in cycle time from weeks to 1–2 days, elimination of pressurized hydrogenation techniques not easily accommodated or handled in conventional reactions, elimination of the isolation of oily or tar products, crystallization of previously uncrystallizable materials, increased purity of product and significant increase in ease of handling. The concatenated synthesis also significantly impacts the ease of crystallization and increased purity of the final drug substance, [1S-[1α,2β,3β,4α(S*)]]-4-[7-[[1-[(3-chlorothien-2yl)methyl]propyl]amino]-3H-imidazo[4,5-b]pyrid-3-yl] N-ethyl 2,3-dihydroxycyclopentane carboxamide.

The foregoing may be better understood by reference to the following Examples, which are presented for purposes of illustration and are not intended to limit the scope of the invention.

EXAMPLE 1

First Concatenated Synthesis of [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate.

A reaction vessel $R_1$ is charged with 11.7 g of (R)-1-(3-chloro-thienyl-2-yl)-2-aminobutane hydrochloride (prepared as described in PCT/US97/15729, incorporated herein by reference), 55 ml of 1-methyl-2-pyrrolidinone and 13.5 ml of N,N-diisopropylethylamine at room temperature. The mixture is stirred. The reaction vessel $R_1$ is then charged with 7 ml of water and 14.4 ml of triethylamine at room temperature. The mixture is stirred and 10.01 g of solid 2,4-dichloro-3-nitropyridine is directly added to reaction vessel $R_1$ at room temperature. The resulting mixture is heated at about 35° C. for 6 hours with stirring. The mixture is cooled to room temperature with stirring over 16 hours.

The reaction vessel $R_1$ is then charged with 19.97 g of 3aR-[3aα,4α,6a,6aα]-6-amino-N-ethyl tetrahydro-3,3-dimethyl-2,4-dioxabicyclo[3.3.0]octan-8-carboxamide, benzoate and 32.5 ml of N,N-diisopropylethylamine. The mixture is heated to about 105° C. and held at that temperature for 5 hours. The mixture is allowed to cool overnight at room temperature. The product of the second reaction is identified as [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide.

The mixture is then cooled to below 15° C. 80 mL of ethyl acetate and 80 mL of water are added and the mixture cooled to 5–10° C. The mixture is stirred for 20 minutes while the temperature is maintained at 5–10° C. Stirring is stopped and the layers are allowed to separate, typically over 15–20 minutes. The lower aqueous layer is removed to a holding drum/reactor vessel.

The ethyl acetate layer is washed once with 40 mL of cold water (5–10° C.). 30 mL of methanol is added to the ethyl acetate reaction mixture in reaction vessel $R_1$ and the mixture is stirred for 10 minutes. 31.9 g of ammonium acetate is added to reaction vessel $R_1$ and the mixture is stirred for 15 minutes. An endotherm is observed upon ammonium acetate addition. 20.3 g of zinc powder is added to reaction mixture $R_1$ in portions until no exotherm is observed. The temperature is maintained to about 50° C.

The mixture in reaction vessel $R_1$ is then cooled to about 22° C. The mixture is filtered onto Whatman filter paper #1 and the filtrate transferred to reaction vessel $R_2$. Reaction vessel $R_1$ is rinsed with ethyl acetate, filtered and the filtrate transferred to reaction vessel $R_2$. The filter cake is washed three times with 50 mL of ethyl acetate and the washes are transferred to reaction vessel $R_2$. 40 mL of concentrated hydrochloric acid is added to reaction vessel $R_2$ and the temperature allowed to rise to about 42° C.

When the hydrolysis reaction is substantially complete, the temperature in reaction vessel $R_2$ is adjusted to about 22° C. and maintained at about 22° C. for 2 hours. The reaction mixture is then filtered through Whatman filter paper #1. The reaction vessel $R_2$ is rinsed with ethyl acetate and the rinse is filtered through the filter paper. 17.89 g of crude [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate is collected on the filter paper. The crude product is washed three times with 35 mL of ethyl acetate and then transferred to a dryer and dried at about 50° C. under vacuum to give [1S-[1α,2β,3β,4α(S*)]]-4-[3-amino-4-[[1-[3-chlorothien-2-yl)methyl]propyl]amino]pyrid-2-ylamino] N-ethyl 2,3-dihydrocyclopentane carboxamide dihydrochloride hydrate (11.69 g, 88.5% w/w assay).

The [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate prepared as described above is converted to [1S-[1α,2β,3β,4α(S*)]]-4-[7-[[1-[(3-chlorothien-2-yl)methyl]propyl]amino]-3H-imidazo[4,5-b]pyrid-3-yl] N-ethyl 2,3-dihydroxycyclopentanecarboxamide as described in PCT/US97/21439, incorporated herein by reference.

Alternatively, the [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate prepared as described above is purified prior to conversion to [1S-[1α,2β,3β,4α(S*)]]-4-[7-[[1-[(3-chlorothien-2-yl)methyl]propyl]amino]-3H-imidazo[4,5-b]pyrid-3-yl] N-ethyl 2,3-dihydroxycyclopentanecarboxamide using the method described below.

11.69 g of [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate, 70 mL of isopropyl alcohol and 70 mL of methanol are added to a reaction vessel. The mixture is heated at about 68° C. for 1 hour. The mixture is then hot filtered (approximately 50° C.) through Whatman filter paper #1. The white solid product is then washed twice with 20 mL of isopropyl alcohol:methanol (1:1) at room temperature. The white solid product is dried in a vacuum oven for 16 hours at about 40° C. to give [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate (6.95 g, 97–100% w/w assay).

EXAMPLE 2

Second Concatenated Synthesis of [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentanecarboxamide dihydrochloride hydrate.

A reaction vessel $R_1$ is charged with 49.0 g of (R)-1-(3-chloro-thienyl-2-yl)-2-aminobutane hydrochloride and 38.2 g of 2,4-dichloro-3-nitropyridine at room temperature. The reaction vessel $R_1$ is further charged with 225 mL of 1-methyl-2-pyrrolidinone, 120.7 mL of N,N-diisopropylethylamine and 32.6 mL of N-methylmorpholine at room temperature with stirring. The reaction vessel $R_1$ is heated at about 72° C. for 8 hours with stirring. The mixture is cooled overnight to room temperature with stirring.

The reaction vessel $R_1$ is then charged with 76.3 g of 3aR-[3aα,4α,6a,6aα]-6-amino-N-ethyl tetrahydro-3,3-dimethyl-2,4-dioxabicyclo[3.3.0]octan-8-carboxamide benzoate. The mixture is heated to about 105° C. and held at that temperature for 7 hours. The mixture is allowed to cool overnight at room temperature. The product of the second reaction is identified as [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide.

The reaction mixture is then cooled to about 25° C. and 300 mL of ethyl acetate and 300 g of ammonium chloride (20%) are added to reaction vessel $R_1$. The mixture is stirred for 10 minutes while at 25° C. Stirring is then stopped and the layers are allowed to separate. The lower aqueous layer is removed to a holding drum/reactor vessel.

150 mL of water is added to the ethyl acetate layer remaining in reaction vessel $R_1$. The mixture is stirred for 10 minutes. Stirring is stopped and the layers are allowed to separate. The lower aqueous layer is removed to the holding drum/reactor vessel.

200 mL of methanol and 91 g of ammonium acetate are added to reaction vessel $R_1$. An exotherm is observed with ammonium acetate addition. 58 g of zinc powder is added to reaction vessel $R_1$ in portions until no exotherm is observed. The temperature in reaction vessel $R_1$ is maintained at 50° C.

When the reduction reaction is substantially complete, the mixture in reaction vessel $R_1$ is cooled to 0° C. The mixture is filtered through Whatman filter paper #1 and the filtrate is transferred to reaction vessel $R_2$. The filter cake is washed three times with 150 mL of ethyl acetate and the washes are transferred to reaction vessel $R_2$. 300 mL of water is added to reaction vessel $R_2$ and the mixture is stirred for 10 minutes. Stirring is stopped and the layers are allowed to separate. The lower aqueous layer is removed to a holding drum/reactor vessel.

The ethyl acetate layer is filtered through Whatman filter paper #1. Reaction vessel $R_2$ is rinsed with ethyl acetate and the rinse and filtrate are transferred to reaction vessel $R_3$. 180 mL of methanol and 154 mL of concentrated hydrochloric acid are added to reaction vessel $R_3$. The reaction is stirred for 2 hours at room temperature during which time an off-white precipitate forms.

The off-white precipitate is isolated by filtration through Whatman filter paper #1 and is washed three times with 150 mL of ethyl acetate. The solid product is dried in a vacuum oven at about 45° C. to provide [1S-[1α,2β,3β,4α(S*)]]-4-[3-amino-4-[[1-[3-chlorothien-2-yl)methyl]propyl]amino] pyrid-2-ylamino] N-ethyl 2,3-dihydroxycyclopentanecarboxamide dihydrochloride hydrate (68 g, 61% yield, 80 A % (HPLC)). MS 470 (M+H). Analysis calculated for $C_{21}H_{30}N_5O_3ClS$ 2HCl $H_2O$: C, 45.13; H, 6.13; N, 12.53; Cl, 19.03. Found: C, 45.14; H, 6.15; N, 12.46; Cl, 19.12.

EXAMPLE 3

Preparation of 2,4-difluoro-3-nitropyridine

A reaction vessel is charged with 1 eq. of 2,4-dichloro-3-nitropyridine, 3.5 eq. of KF, 0.05 eq. of 18-crown-6 and 1-methyl-2-pyrrolidinone. The mixture is heated at 100° C. for 15 hours and then cooled to 22° C. Ethyl acetate is added to the reaction vessel and the mixture stirred for 15 minutes. The mixture is washed with water and then with brine. The ethyl acetate layer is dried with magnesium sulfate and the ethyl acetate removed under reduced pressure to provide the title compound.

EXAMPLE 4

Third Concatenated Synthesis of [1S-[1α,2β,3β,4α(S*)]]-4-[3-amino-4-[[1-[3-chlorothien-2-yl)methyl]propyl]amino] pyrid-2-ylamino] N-ethyl 2,3-dihydroxycyclopentanecarboxamide dihydrochloride hydrate.

A reaction vessel is charged with 1 eq. of (R)-1-(3-chloro-thienyl-2-yl)-2-aminobutane hydrochloride, 1.05 eq. of 2,4-difluoro-3-nitropyridine and 1-methyl-2-pyrrolidinone. The reaction mixture is cooled to −10° C. and N-methylmorpholine added. The reaction is complete at the end of the addition. The reaction mixture is warmed to 22° C. and 1.1 eq. of 3aR-[3aα,4α,6α,6aα]-6-amino-N-ethyltetrahydro-3,3-dimethyl-2,4-dioxabicyclo[3.3.0]octan-8-carboxamide benzoate is added and the reaction mixture is heated at 100° C. for 1 hour.

The reaction mixture is cooled to about 22° C. and ethyl acetate and 20% ammonium chloride are added. The mixture is stirred, the layers are allowed to separate and the lower aqueous layer is removed. The organic layer is washed with water and then methanol followed by ammonium acetate are added. The mixture is stirred for 15 minutes. Zinc powder is added to the reaction mixture until no exotherm is observed. The temperature of the reaction mixture is maintained at about 50° C.

The reaction mixture is then cooled to 0° C. and filtered. The reaction vessel and filter cake are washed with ethyl acetate. The filtrate is washed with water and filtered. Methanol and concentrated hydrochloric acid are added to the organic layer and the reaction temperature is allowed to rise to about 45° C. The mixture is cooled to 22° C. and left standing for two hours. The reaction mixture is then filtered and the reaction vessel and filter cake are rinsed with ethyl acetate. The solid product is dried at 45° C. under 25 mm Hg until constant weight, typically about 3 hours, to provide the title compound as an off-white solid (69% yield, 94 A % (HPLC)). MS 468, 470 (100) (M+H, Cl pattern). Elemental analysis calculated for $C_{21}H_{30}N_5O_3ClS$ 2HCl $H_2O$: C, 45.13; H, 6.13; N, 12.53; Cl, 19.03; S, 5.74. Found: C, 45.11; H, 6.03; N, 12.41; Cl, 19.16; S, 5.98.

EXAMPLE 5

Fourth Concatenated Synthesis of [1S-[1α,2β,3β,4α(S*)]]-4-[3-amino-4-[[1-[3-chlorothien-2-yl)methyl]propyl] amino]pyrid-2-ylamino] N-ethyl 2,3-dihydroxycyclopentanecarboxamide dihydrochloride hydrate.

10.5 g of KF, 3.2 g of tetraphenylphosphonium bromide, 33 mL of 1-methyl-2-pyrrolidinone and 130 mL of toluene are added to a 250 mL round bottom flask. The bulk of the toluene is distilled off at reduced pressure (80 mbar, 60–70° C.) to remove residual moisture (110 mL collected), after which the slurry is cooled to 24° C. under nitrogen. 10 g (0.052 mole) of 2,4-dichloro-3-nitropyridine is added and the mixture heated to 100° C. with stirring under a nitrogen. After approximately 10 hours, HPLC analysis shows completely conversion to 2,4-difluoro-3-nitropyridine.

The reaction mixture is then cooled to 0° C. and 26.2 g (0.26 mole) of 4-methylmorpholine added. A solution of 10.6 g (0.047 mole) of (R)-1-(3-chloro-thienyl-2-yl)-2-aminobutane, hydrochloride in 15 mL of 1-methyl-2-pyrrolidinone is added dropwise to the reaction mixture while holding the temperature between 5 and 0° C. with a salt water ice bath. By the end of the addition, HPLC analysis indicates complete conversion of 2,4-difluoro-3-pyridine to the aminated product.

The reaction is allowed to warm to 24° C. 17.0 g (0.048) of 3aR-[3aα,4α,6α,6aα]-6-amino-N-ethyl tetrahydro-3,3-dimethyl-2,4-dioxabicyclo[3.3.0]octan-8-carbox-amide benzoate is added and the mixture heated at 90° C. for 4 hours. After 4 hours, HPLC analysis indicates complete conversion to [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide. The reaction mixture is cooled to 24° C., diluted with 80 mL of ethyl acetate and washed with 80 mL of 20% aqueous ammonium chloride solution. The aqueous phase is separated and removed. The organic phase is washed with 40 mL of water. Following the removal of the aqueous phase, 24 mL of methanol is added to the organic phase followed by the addition of 27.0 g (0.35 mole) of ammonium acetate. The mixture is cooled to 5° C. in an ice bath. 17 g (0.26 mole) of zinc dust is added in portions while maintaining the reaction temperature below 40° C. This addition is exothermic. Following the addition, the deep yellow color of the reaction mixture turns a light amber color and a grayish precipitate forms. TLC analysis at this point shows complete reduction.

The mixture is cooled to 0° C. and filtered to remove zinc salts. The filter cake is washed three times with 40 mL of ethyl acetate and the combined filtrate and washes are washed with 80 mL of water. Some additional inorganic precipitate forms during this process and is removed by filtration. Following phase separation, 27 mL of methanol is added to the organic phase, followed by 33 mL of concentrated HCl. The temperature of the mixture raised to 40° C. The mixture is then allowed to cool to 24° C. over 3 hours, after which HPLC analysis shows that the acetonide deprotection is complete.

The mixture is cooled to 0° C. and a solid tan precipitate is isolated by filtration. The reaction flask and filter cake are washed 3 times with 30 mL of cold (5° C.) ethyl acetate. The solid is then dried in a vacuum oven (45° C., 27 mm Hg) to constant weight (4 hours) to provide the title compound (22.9 g, 79% based on 2,4-dichloro-3-nitropyridine) as an off white solid. Analysis calculated for $C_{21}H_{34}Cl_3N_5O_4S_1$; C, 45.13; H, 6.13; N, 12.53; S, 5.74; Cl 19.03. Found: C, 45.32; H, 6.31; N, 12.24; S, 5.86; Cl 18.90.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and articles cited herein are hereby incorporated by reference in their entirety and relied upon.

What is claimed is:

1. A process for preparing a 2-halo-3-nitro-4-aminopyridine compound of formula

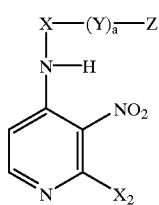

wherein X is a straight or branched chain alkylene, cycloalkylene or cycloalkenylene group; $X_2$ is Cl or F; Y is $NR_4$, O or S; a=0 or 1; Z is of the formula

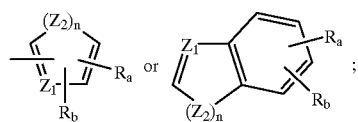

wherein $Z_1$ is N, $CR_5$, $(CH)_m$-$CR_5$ or $(CH)_m$-N, m being 1 or 2; and $Z_2$ is N, $NR_6$, O or S, n being 0 or 1;

$R_4$, $R_5$ and $R_6$ are independently H, alkyl, aryl or heterocyclyl; and $R_a$ and $R_b$ are independently H, OH, alkyl, hydroxyalkyl, alkyl mercaptyl, thioalkyl, alkoxy, alkoxyalkyl, amino, alkyl amino, carboxyl, acyl, halogen, carbamoyl, alkyl carbamoyl, aryl or heterocyclyl;

comprising reacting a 2,4-dihalo-3-nitropyridine compound of formula

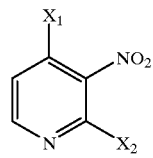

wherein $X_1$ is F and $X_2$ is Cl or F with an amine of formula $H_2N$—X-$(Y)_a$-Z.

2. The process of claim 1 wherein both $X_1$ and $X_2$ are F.

3. The process of claim 1 wherein X is a straight or branched chain alkylene; a=0; $R_4$, $R_5$ and $R_6$ are independently H or alkyl; and Z is

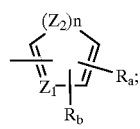

wherein $Z_1$ is N, $CR_5$, $(CH)_m$-$CR_5$ or $(CH)_m$-N, m being 1 or 2; and $Z_2$ is N, $NR_6$, O or S, n being 0 or 1.

4. The process of claim 1 wherein $H_2N$—X—$(Y)_a$-Z is (R)-1-(3-chlorothien-2-yl)-2-aminobutane.

5. The process of claim 1, further comprising the step of reacting the 2-halo-3-nitro-4-aminopyridine compound with a protected dihydroxyaminocyclopentane compound of formula

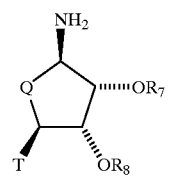

to form a 2,4-diamino-3-nitropyridine compound of formula

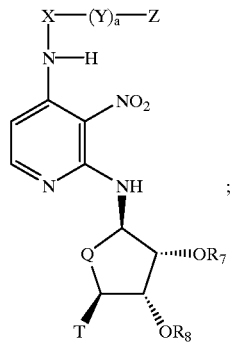

;

wherein T is

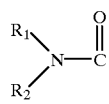

or $R_3O$—$CH_2$; Q is $CH_2$ or O; $R_1$, $R_2$ and $R_3$ are independently H, alkyl, aryl or heterocyclyl; and $R_7$ and $R_8$ are independently hydrogen, alkyl, aralkyl, carbamoyl, alkyl carbamoyl, dialkyl-carbamoyl, acyl, alkoxy-carbonyl, aralkoxycarbonyl, aryloxycarbonyl, or $R_7$ or $R_8$ together form

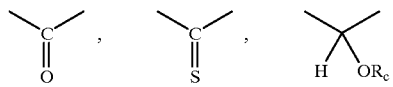

where $R_c$ is hydrogen or alkyl,

where $R_d$ and $R_e$ are independently hydrogen, alkyl, or together with the carbon atom they are attached to form a 1,1-cycloalkyl group.

6. The process of claim 5 wherein Q is $CH_2$; $R_1$ and $R_2$ are independently H or alkyl;
T is

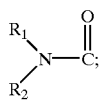

and $R_7$ and $R_8$ are alkyl, or together form

where $R_d$ and $R_e$ are in-dependently hydrogen or alkyl, or together with the carbon atom they are attached to form a 1,1-cycloalkyl group.

7. The process of claim 5, further comprising the step of reducing the 2,4-diamino-3-nitropyridine compound to form a 2,3,4-triaminopyridine compound of formula

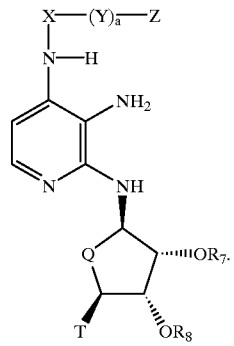

8. The process of claim 7, further comprising the step of removing the groups $R_7$ and $R_8$.

9. The process of claim 8, further comprising the step of reacting the 2,3,4-triaminopyridine compound with an orthoformate ester, formamidine acetate or dimethylformamide dimethyl acetal to form a compound of formula

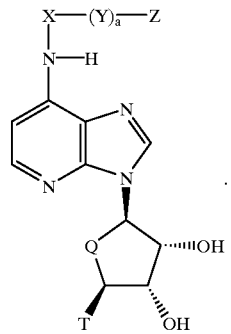

10. A process for preparing (R)-N-[1-[(3-chlorothien-2-yl)methyl]propyl]-2-halo-3-nitro-4-pyridinamine comprising (a) reacting a 2-halo-4-fluoro-3-nitropyridine, wherein halo is Cl or F with (R)-1-(3-chlorothien-2-yl)-2-aminobutane, hydrochloride.

11. The process of claim 10, further comprising the step of (b) reacting the (R)-N-[1-[(3-chlorothien-2-yl)methyl]propyl]-2-halo-3-nitro-4-pyridinamine with 3aR-[3aα,4α,6α,6aα]-6-amino-N-ethyl tetrahydro-3,3-di-methyl-2,4-dioxabicyclo[3.3.0]octan-8-carboxamide, benzoate to form [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide.

12. The process of claim 11, further comprising the step of (c) reducing the [3aR-[3aα,4α,6a(R*),6aα]]-6-[4-[[1-[(3-chlorothien-2-yl)methyl]propyl]amino]-3-nitropyrid-2-ylamino] N-ethyl tetrahydro-2,2-dimethyl-4H-cyclopenta-1,3-dioxole-4-carboxamide to form [3aR-[3aα,4α,6(R*),6aα]]-6-[4-[[1-[(3-chlorothien-2-yl)methyl]propyl]amino]-3-aminopyrid-2-ylamino] N-ethyl tetrahydro-2,2-dimethyl-4H-cyclopenta-1,3-dioxole-4-carboxamide.

13. The process of claim 12, further comprising the step of (d) hydrolyzing the [3aR-[3aα,4α,6a(R*),6aα]]-6-[4-[[1-[(3-chlorothien-2-yl)methyl]propyl]amino]-3-aminopyrid-2-ylamino] N-ethyl tetrahydro2,2-di-methyl-4H-cyclopenta-1,3-dioxide-4-carboxamide to form [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentane carboxamide dihydrochloride hydrate.

14. The process of claim 13, further comprising the step of recovering the [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentane carboxamide dihydrochloride hydrate.

15. The process of claim 14, further comprising the step of reacting the [1S-[1α,2β,3β,4α(S*)]]-4-[3-amino-4-[[1-[3-chlorothien-2-yl)methyl]propyl]amino]pyrid-2-ylamino] N-ethyl 2,3-dihydroxycyclopentane carboxamide dihydrochloride hydrate with an orthoformate ester, formamidine acetate or dimethylformamide dimethyl acetal to form [1S-[[1α,2β,3β,4α(S*)]]-4-[7-[[1-[(3-chlorothien-2-yl)methyl] propyl]amino]-3H-imidazo[4,5-b]pyrid-3-yl] N-ethyl 2,3-dihydroxycyclopentane carboxamide.

16. The process of claim 13, wherein said steps (a)–(d) are effected in a concatenated manner without isolation of the intermediate compounds (R)-N-[1-[(3-chlorothien-2-yl) methyl]propyl]-2-halo-3-nitro-4-pyridinamine, [3aR-[3aα, 4α,6a(R*),6aα]]-6-[4-[[1-(3-chlorothien-2-yl)methyl] propyl]amino]-3-nitropyrid-2-ylamino] N-ethyl tetrahydro-2,2-dimethyl-4H-cyclopenta-1,3-dioxole-4-carboxamide and [3aR-[3aα,4α,6a(R*),6aα]]-6-[4-[[1-[(3-chlorothien-2-yl)methyl]propyl]amino]-3-aminopyrid-2-ylamino] N-ethyl tetrahydro-2,2-dimethyl-4H-cyclopenta-1,3-dioxole-4-carboxamide.

17. The process of claim 16 wherein the 2,4-dihalo-3-nitropyridine is 2,4-difluoro-3-nitropyridine or a mixture of 2,4-difluoro-3-nitropyridine and 2-chloro-4-fluoro-3-nitropyridine.

18. The process of claim 16 further comprising the step of converting 2,4-dichloro-3-nitropyridine to a mixture of 2,4-difluoro-3-nitropyridine and 2-chloro-4-fluoro-3-nitropyridine.

* * * * *